United States Patent [19]

Muto et al.

[11] Patent Number: 4,495,192
[45] Date of Patent: Jan. 22, 1985

[54] 1-SUBSTITUTED 1,4-DIHYDROPYRIDINES

[75] Inventors: Kenji Muto; Yoshinori Takemoto, both of Shizuoka; Takao Hatta, Sagamihara; Tamotsu Hashimoto, Numazu; Koji Yamada, Susono; Minoru Watanabe, Tokyo, all of Japan

[73] Assignee: Kyowa Hakko Kogyo Co., Ltd., Tokyo, Japan

[21] Appl. No.: 490,167

[22] Filed: Apr. 29, 1983

[30] Foreign Application Priority Data

Apr. 30, 1982 [JP] Japan ................. 57-71425

[51] Int. Cl.³ ................. A61K 31/455; C07D 211/94; C07D 401/12; C07D 405/12
[52] U.S. Cl. ..................... 514/318; 546/321; 546/194; 546/268; 546/281; 546/283; 546/284; 514/929; 514/336; 514/356
[58] Field of Search ............... 546/321, 281, 194, 268, 546/283, 284; 424/266, 267

[56] References Cited

U.S. PATENT DOCUMENTS 3,966,948 6/1976 Bossert et al. ............ 424/266
4,145,432 3/1979 Sato ...................... 546/321
4,393,070 7/1983 Sato et al. ............... 546/321

OTHER PUBLICATIONS

Kurbatova, et al., "Chemistry of Heterocyclic N-Oxides and Related Compounds", Chem. Abstracts 91:91466z.

Primary Examiner—Alan L. Rotman
Assistant Examiner—Dale A. Bjorkman
Attorney, Agent, or Firm—Antonelli, Terry & Wands

[57] ABSTRACT

A vasodilating or anti-hypertensive composition comprises a pharmaceutical carrier and an effective amount of a 1,4-dihydropyridine compound as an active ingredient. The 1,4-dihydropyridine compound may be represented by the following general formula:

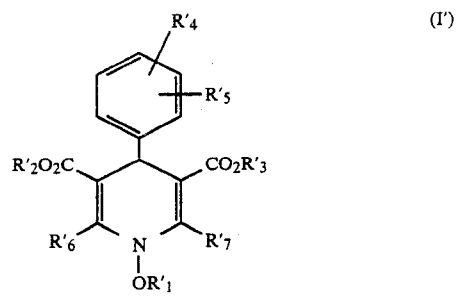

wherein $R'_1$ and $R'_4$ represent a hydrogen atom, $R'_2$ and $R'_3$ represent an alkyl group having 1-5 carbon atoms or a substituted heterocyclic group wherein a substituent is an N-benzylpiperidyl group, $R'_5$ represents a nitro group, and $R'_6$ and $R'_7$ represent an alkyl group having 1-5 carbon atoms.

27 Claims, No Drawings

1-SUBSTITUTED 1,4-DIHYDROPYRIDINES

The present invention relates to 1,4-dihydropyridine derivatives. More specifically, the present invention relates to a 1,4-dihydropyridine compound of the general formula:

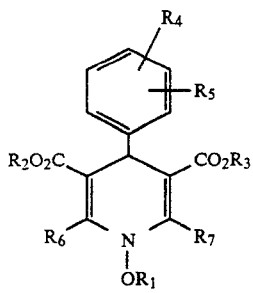

wherein $R_1$ represents a hydrogen atom, an alkyl group having 1-5 carbon atoms, an alkenyl group having 2-5 carbon atoms, an aralkyl group having 7-13 carbon atoms or an acyl group having 1-7 carbon atoms, $R_2$ and $R_3$ are the same or different groups and each represents a substituted or unsubstituted alkyl group having 1-5 carbon atoms, an alkenyl group having 2-5 carbon atoms, a disubstituted aminoalkyl group having 1-5 carbon atoms or a substituted or unsubstituted heterocyclic group, $R_4$ and $R_5$ are the same or different groups and each represents a hydrogen atom, a halogen atom or a nitro group, and $R_6$ and $R_7$ are the same or different groups and each represents an alkyl group having 1-5 carbon atoms, a pharmaceutically acceptable acid addition salt thereof and a pharmaceutical composition containing, as the active ingredient, a 1,4-dihydropyridine compound of the general formula (I).

There has always been a need for the development of excellent drugs for cardiovascular disease having hypotensive and vasodilating activities. The present inventors, as the result of extensive studies for this purpose, have found that a 1,4-dihydropyridine compound of the general formula (I) and pharmaceutically acceptable acid salts thereof are compounds which have excellent effects to dilate coronary artery and peripheral blood vessels and to depress the blood pressure and which are useful as drugs for cardiovascular disease, such as hypotensives, vasodilators etc., and thus have accomplished the present invention.

In the general formula (I), the alkyl group having 1-5 carbon atoms for $R_1$, $R_2$, $R_3$, $R_6$ and $R_7$ includes a methyl group, an ethyl group, a propyl group, a butyl group, a pentyl group etc., the alkenyl group having 2-5 carbon atoms for $R_1$, $R_2$ and $R_3$ includes a vinyl group, an allyl group, a methallyl group etc., the aralkyl group having 7-13 carbon atoms for $R_1$ includes a benzyl group, a phenethyl group, a diphenylmethyl group, the acyl group having 1-7 carbon atoms for $R_1$ includes a formyl group, an acetyl group, a pivaloyl group, a benzoyl group etc., and the halogen atom for $R_4$ and $R_5$ includes a fluorine atom, a chlorine atom, a bromine atom or an iodine atom. Substituents for the substituted alkyl group having 1-5 carbon atoms for $R_2$ and $R_3$ include a halogen atom such as a fluorine atom, a chlorine atom, a bromine atom and an iodine atom or an alkoxy group having 1-5 carbon atoms such as a methoxy group, an ethoxy group, a propoxy group, a butoxy group, etc., and examples of the substituted alkyl group are a methoxyethyl group, an ethoxyethyl group, an n-propoxyethyl group, an isopropoxyethyl group, a fluoroethyl group, a chloroethyl group, a bromoethyl group, an iodoethyl group, a chloropropyl group, a bromopropyl group, an iodopropyl group etc.

The aminoalkyl group having 1-5 carbon atoms in the disubstituted aminoalkyl group having 1-5 carbon atoms for $R_2$ and $R_3$ includes an aminoethyl group, an aminopropyl group etc., and substituents, which are the same or different groups, include alkyl groups having 1-5 carbon atoms such as a methyl group, an ethyl group, a propyl group, a butyl group etc. and aralkyl groups such as a benzyl group etc., and examples of the disubstituted aminoalkyl group having 1-5 carbon atoms are an N,N-dimethylaminoethyl group, an N,N-diethylaminoethyl group, an N-methyl-N-benzylaminoethyl group, an N-ethyl-N-benzylaminoethyl group, an N,N-dimethylaminopropyl group, an N-methyl-N-benzylaminopropyl group etc.

The unsubstituted heterocyclic group for $R_2$ and $R_3$ includes a thienyl group, a furyl group, a piperidyl group, a pyranyl group, a pyrrolidinyl group etc.

Substituents for the substituted heterocyclic group include a hydrogen atom, an alkyl group having 1-5 carbon atoms such as a methyl group, an ethyl group, a propyl group etc., an aralkyl group having 7-8 carbon atoms such as a benzyl group, a phenethyl group etc., and an acyl group having 1-7 carbon atoms such as a formyl group, an acetyl group, a benzoyl group etc., and examples of the substituted heterocyclic group are a tetrahydrofuryl group, a tetrahydrothienyl group, a tetrahydrothiopyranyl group, a thienylmethyl group, a thienylethyl group, an N-methylpiperidyl group, an N-ethylpiperidyl group, an N-isopropylpiperidyl group, an N-benzylpiperidyl group, an N-phenethylpiperidyl group, an N-formylpiperidyl group, an N-acetylpiperidyl group, an N-benzoylpiperidyl group, an N-methylpyrrolidinyl group, an N-ethylpyrrolidinyl group etc.

The pharmaceutically acceptable acid addition salt of the 1,4-dihydropyridine compound of the general formula (I) is selected from the group consisting of inorganic acid salts such as hydrochloride, hydrobromide, phosphate, sulfate, etc. and organic acid salt such as formate, acetate, fumarate, maleate, malate, aspartate, glutamate, etc.

Representative processes for production of the compounds of the present invention are illustrated below.

PROCESS 1

The present compound of the general formula (Ia) (referred to as Compound Ia), i.e. a 1-hydroxy-1,4-dihydropyridine compound may be produced by reacting a 1,5-diketone compound of the general formula (II) (referred to as Compound II) with hydroxylamine.

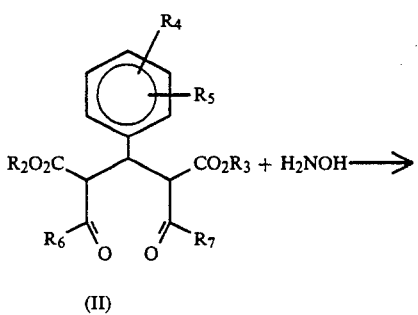

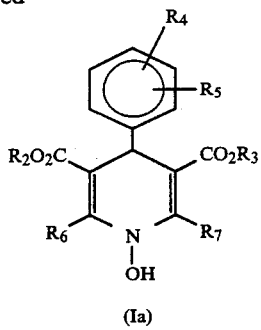

wherein $R_2$, $R_3$, $R_4$, $R_5$, $R_6$ and $R_7$ have the same meaning as defined above.

The mixing molar ratio of Compound II and hydroxylamine is 1.0:0.8–1.0:2.0, preferably 1.0:1.0–1.0:1.3.

The reaction is carried out in the presence or absence of an alcohol such as methanol, ethanol, isopropanol etc., an aromatic hydrocarbon such as benzene, toluene etc., a halogenated hydrocarbon such as dichloromethane, chloroform, carbon tetrachloride etc., an ether such as diethyl ether, tetrahydrofuran, dioxane, 1,2-dimethoxyethane etc., an ester such as ethyl acetate, butyl acetate etc., an aprotic polar solvent such as acetonitrile, dimethylformamide, dimethylsulfoxide etc., or water or the like, at −20° C. to 150° C., preferably at 0° C. to 50° C. Separation of the desired product from the reaction mixture may be effected by conventional operations such as concentration, extraction, column chromatography, crystallization etc.

Compound II employed as the starting material in the present process may be obtained by the following process (i) or (ii).

(i) A process for the Production by Reaction of Aldehyde (III) with Acylacetic Acid Ester (IV)

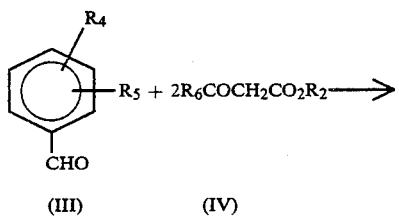

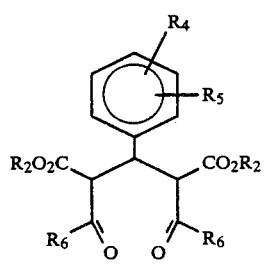

(the present compound represented by the general formula (I) wherein $R_2 = R_3$ and $R_6 = R_7$)
(II)

wherein $R_2$, $R_4$, $R_5$ and $R_6$ have the same meaning as defined above.

The mixing molar ratio of Compound III and Compound IV is 1.0:1.5–1.0:4.0, preferably 1.0:2.0–1.0:2.5. The reaction is carried out in the presence or absence of a solvent, for example, ethers such as diethyl ether, 1,2-dimethoxyethane, tetrahydrofuran, dioxane etc., halogenated hydrocarbons such as dichloromethane, chloroform, carbon tetrachloride etc., esters such as ethyl acetate, butyl acetate etc. and the like, using, as a catalyst, a Lewis acid such as zinc chloride, tin tetrachloride, boron trifluoride, titanium tetrachloride, aluminum chloride etc. at 0° C. to 100° C., preferably at 20° C. to 80° C.

(ii) A process for the Production by Reaction of Benzylideneacylacetic Acid Ester (V) with Acylacetic Acid Ester (IV)

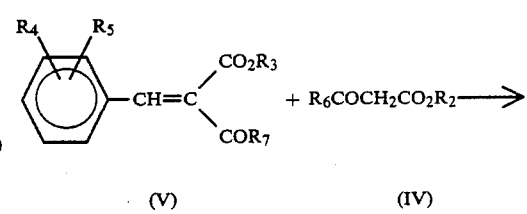

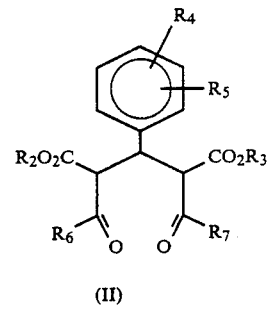

wherein $R_2$, $R_3$, $R_4$, $R_5$, $R_6$ and $R_7$ having the same meaning as defined above.

The mixing molar ratio of Compound V and the Compound IV is 1.0:0.8–1.0:8.0, preferably 1.0:1.0–1.0:6.0. The reaction is carried out in the presence or absence of a solvent, for example, aromatic hydrocarbons such as benzene, toluene, xylene etc., ethers such as diethyl ether, 1,2-dimethoxyethane, tetrahydrofuran, dioxane etc., alcohols such as methanol, ethanol etc. and the like, using, as a catalyst, a fluoride such as potassium fluoride, cesium fluoride etc. at −20° C. to 140° C., preferably at 0° C. to 60° C.

Both of Compound IV and Compound V employed as the starting materials in the present process are either known compounds which may be produced by a known process [A. B. Boese, Ind. Eng. Chem., 32, 16 (1940); G. Jones, "The Knoevenagel Condensation", Org. Reaction, XV, 204 (1967) etc.].

PROCESS 2

The present compounds other than Compounds Ia according to Process 1, may be obtained by o-alkylating or o-acylating Compound Ia with an alkylating agent such as dimethyl sulfate, benzyl chloride, phenethyl bromide, allyl chloride, allyl bromide, methyl iodide etc. or an acylating agent such as acetyl chloride, benzoyl chloride, etc.

Typical examples of the present compound are listed below. The structure, melting point and NMR of each of these compounds are set forth in Table 1.

| Compound No. | Name of Compound |
|---|---|
| 1 | 1-Hydroxy-2,6-dimethyl-4-(3-nitrophenyl)-1,4-dihydropyridine-3,5-dicarboxylic acid dimethyl ester |
| 2 | 1-Hydroxy-2,6-dimethyl-4-(3-nitrophenyl)-1,4-dihydropyridine-3,5-dicarboxylic acid diethyl ester |
| 3 | 4-(4-Chloro-3-nitrophenyl)-1-hydroxy-1,4-dihydropyridine-3,5-dicarboxylic acid dimethyl ester |
| 4 | 1-Hydroxy-2,6-dimethyl-4-(3-nitrophenyl)-1,4-dihydropyridine-3,5-dicarboxylic acid 3-isopropyl-5-methyl ester |
| 5 | 1-Hydroxy-2,6-dimethyl-4-(3-nitrophenyl)-1,4-dihydropyridine-3,5-dicarboxylic acid 3-ethyl-5-methyl ester |
| 6 | 1-Hydroxy-2,6-dimethyl-4-(3-nitrophenyl)-1,4-dihydropyridine-3,5-dicarboxylic acid 3-methyl-5-n-propyl ester |
| 7 | 1-Hydroxy-2,6-dimethyl-4-(3-nitrophenyl)-1,4-dihydropyridine-3,5-dicarboxylic acid 3-isobutyl-5-methyl ester |
| 8 | 1-Hydroxy-2,6 dimethyl-4-(3-nitrophenyl)-1,4-dihydropyridine-3,5-dicarboxylic acid 3-ethyl-5 isopropyl ester |
| 9 | 1-Hydroxy-2,6-dimethyl-4-(3-nitrophenyl)-1,4-dihydropyridine-3,5-dicarboxylic acid 3-allyl-5-methyl ester |
| 10 | 1-Hydroxy-2,6-dimethyl-4-(3-nitrophenyl)-1,4-dihydropyridine-3,5-dicarboxylic acid 3-methoxyethyl-5-methyl ester |
| 11 | 1-Hydroxy-2,6-dimethyl-4-(3-nitrophenyl)-1,4-dihydropyridine-3,5-dicarboxylic acid 3-methyl-5-(3-tetrahydrofuryl) ester |
| 12 | 1-Hydroxy-2,6-dimethyl-4-(3-nitrophenyl)-1,4-dihydropyridine-3,5-dicarboxylic acid 3-methyl-5-[2-(2-thienyl)ethyl] ester |
| 13 | 1-Hydroxy-2,6-dimethyl-4-(3-nitrophenyl)-1,4-dihydropyridine-3,5-dicarboxylic acid 3-(2-chloroethyl)-5-methyl ester |
| 14 | 1-Hydroxy-2,6-dimethyl-4-(3-nitrophenyl)-1,4-dihydropyridine-3,5-dicarboxylic acid 3-(1-formyl-4-piperidyl)-5-methyl ester |
| 15 | 1-Hydroxy-2,6-dimethyl-4-(3-nitrophenyl)-1,4-dihydropyridine-3,5-dicarboxylic acid 3-(1-formyl-3-piperidyl)-5-methyl ester |
| 16 | 4-(2,3-dichlorophenyl)-1-hydroxy-2,6-dimethyl-1,4-dihydropyridine-3,5-dicarboxylic acid 3-isopropyl-5-methyl ester |
| 17 | 1-Hydroxy-2,6-dimethyl-4-(3-nitrophenyl)-1,4-dihydropyridine-3,5-dicarboxylic acid-3-methyl-5-(4-piperidyl) ester |
| 18 | 1-Hydroxy-2,6-dimethyl-4-(3-nitrophenyl)-1,4-dihydropyridine-3,5-dicarboxylic acid-3-methyl-5-(3-piperidyl) ester |
| 19 | 1-Hydroxy-2,6-dimethyl-4-(3-nitrophenyl)-1,4-dihydropyridine-3,5-dicarboxylic acid 3-(1-benzyl-4-piperidyl)-5-methyl ester hydrochloride |
| 20 | 1-Hydroxy-2,6-dimethyl-4-(3-nitrophenyl)-1,4-dihydropyridine-3,5-dicarboxylic-acid-3-(1-benzyl-3-piperidyl)-5-methyl ester hydrochloride |
| 21 | 1-Hydroxy-2,6-dimethyl-4-(3-nitrophenyl)-1,4-dihydropyridine-3,5-dicarboxylic acid-3-[2-(N—benzyl-N—methylamino)ethyl] ester-5-methyl ester hydrochloride |
| 22 | 2,6-Dimethyl-1-methoxy-4-(3-nitrophenyl)-1,4-dihydropyridine-3,5-dicarboxylic acid dimethyl ester |
| 23 | 1-Benzyloxy-2,6-dimethyl-4-(3-nitrophenyl)-1,4-dihydropyridine-3,5-dicarboxylic acid dimethyl ester |
| 24 | 1-Allyloxy-2,6-dimethyl-4-(3-nitrophenyl)-1,4-dihydropyridine-3,5-dicarboxylic acid dimethyl ester |
|  | 1-Acetoxy-2,6-dimethyl-4-(3-nitrophenyl)-1,4-dihydropyridine-3,5-dicarboxylic acid dimethyl ester |

TABLE 1

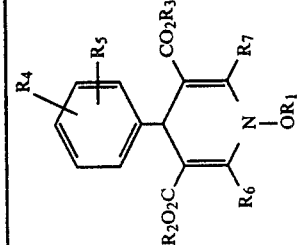

| Compound No. | R₁ | R₂ | R₃ | R₄ | R₅ | R₆ | R₇ | m.p. °C. | NMR·δ |
|---|---|---|---|---|---|---|---|---|---|
| 1 | H | CH₃ | CH₃ | H | 3-NO₂ | CH₃ | CH₃ | 139-140 | CDCl₃:2.52(6H,s), 3.68 (6H,s), 5.16(1H,s), 7.17-8.07(4H,m), 8.18(1H,s) |
| 2 | H | CH₂CH₃ | CH₂CH₃ | H | 3-NO₂ | CH₃ | CH₃ | 83-84 | CDCl₃:1.24(6H,t), 2.50(6H,s) 4.11(4H,q), 5.15(1H,s), 7.1-8.1(4H,m), 8.43(1H,s) |
| 3 | H | CH₃ | CH₃ | 4-Cl | 3-NO₂ | CH₃ | CH₃ | 158-158.5 | DMSO—d₆:2.48(6H,s), 3.64 (6H,s), 5.10(1H,s), 7.5-7.8(3H,m), 10.44(1H,s) |
| 4 | H | CH₃ | CH(CH₃)₂ | H | 3-NO₂ | CH₃ | CH₃ | 116-117 | DMSO—d₆:1.20(6H,d), 2.46(3H,s), 2.48(3H,s), 3.61(3H,s), 4.94(1H,m), 5.10(1H,s), 7.4-8.2 (4H,m), 10.50(1H,s) |
| 5 | H | CH₃ | CH₂CH₃ | H | 3-NO₂ | CH₃ | CH₃ | 123-124 | CDCl₃:1.25(3H,t), 2.50(6H,s), 3.66(3H,s), 4.12(2H,q), 5.14(1H,s), 7.2-8.1(4H,m), 8.20(1H,s) |
| 6 | H | CH₃ | CH₂CH₂CH₃ | H | 3-NO₂ | CH₃ | CH₃ | 101-102 | DMSO—d₆:0.85(3H,t), 1.3-1.9 (2H,m), 2.50(6H,s), 3.64 (3H,s), 4.03(2H,t), 5.16 (1H,s), 7.5-8.2(4H,m), 10.52(1H,s) |
| 7 | H | CH₃ | CH₂CH(CH₃)₂ | H | 3-NO₂ | CH₃ | CH₃ | (oily form) | DMSO—d₆:0.84(6H,d), 1.6-2.2 (1H,m), 2.44(3H,s), 2.48 (3H,s), 3.61(3H,s), 3.82 (2H,d), 5.13(1H,s), 7.5-8.2 (4H,m), 10.48(1H,s) |
| 8 | H | CH₂CH₃ | CH(CH₃)₂ | H | 3-NO₂ | CH₃ | CH₃ | 136-137 | CDCl₃:1.0-1.5(9H,m), 2.50 (6H,broad), 4.10(2H,q), 4.7-5.3(2H,m), 7.2-8.1 (5H,m) |
| 9 | H | CH₃ | CH₂CH=CH₂ | H | 3-NO₂ | CH₃ | CH₃ | 119-120 | DMSO—d₆:2.50(6H,s), 3.65 (3H,s), 4.5-4.7(2H,m) |

TABLE 1-continued

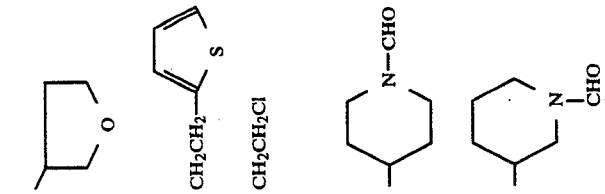

| Compound No. | $R_1$ | $R_2$ | $R_3$ | $R_4$ | $R_5$ | $R_6$ | $R_7$ | m.p. °C. | NMR · δ |
|---|---|---|---|---|---|---|---|---|---|
| 10 | H | $CH_3$ | $CH_2CH_2OCH_3$ | H | 3-$NO_2$ | $CH_3$ | $CH_3$ | 116–118 | 5.0–5.5(3H,m), 5.6–6.3 (1H,m), 7.5–8.2(4H,m), 10.56(1H,s) |
| 11 | H | $CH_3$ | 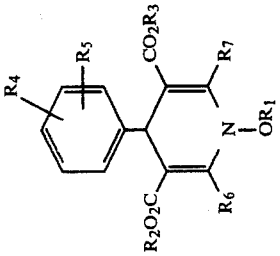 | H | 3-$NO_2$ | $CH_3$ | $CH_3$ | 140 | DMSO—$d_6$:2.48(6H,s), 3.24 (3H,s), 3.3–3.8(5H,m), 4.1–4.3(2H,m), 5.14(1H,s), 7.4–8.2(4H,m), 10.53(1H,s) |
| 12 | H | $CH_3$ | (thiophene-$CH_2CH_2$) | H | 3-$NO_2$ | $CH_3$ | $CH_3$ | (amorphous) | DMSO—$d_6$:1.7–2.2(2H,m), 2.48 (6H,s), 3.5–4.0(7H,m), 5.0–5.4(2H,m), 7.5–8.2 (4H,m), 10.53(1H,s) |
| 13 | H | $CH_3$ | $CH_2CH_2Cl$ | H | 3-$NO_2$ | $CH_3$ | $CH_3$ | (amorphous) | $CDCl_3$:2.48(6H,s), 3.14(2H,t), 3.65(3H,s), 4.29(2H,t), 5.17(1H,s), 6.7–8.2(7H,m), 8.43(1H,s) |
| 14 | H | $CH_3$ | (4-N-CHO-piperidinyl) | H | 3-$NO_2$ | $CH_3$ | $CH_3$ | (amorphous) | $CDCl_3$:2.53(6H,s), 3.4–3.9(5H,m), 4.33(2H,s), 5.17(1H,s), 7.3–8.2 (4H,m), 8.33(1H,s) |
| 15 | H | $CH_3$ | (3-N-CHO-piperidinyl) | H | 3-$NO_2$ | $CH_3$ | $CH_3$ | (amorphous) | DMSO—$d_6$:1.2–2.0(4H,broad), 2.50 (6H,s), 3.0–3.9(4H,broad), 3.63(3H,s), 4.7–5.3(1H,broad), 5.17(1H,s), 7.4–8.2(5H,m), 10.59(1H,s) |
|  |  |  |  |  |  |  |  |  | DMSO—$d_6$:1.1–2.0(4H,broad), 2.49 (6H,s), 2.7–4.0(4H,broad), 3.64(3H,s), 4.6–5.0(1H,broad), 5.14(1H,s), 7.3–8.3(5H,m), 10.55(1H,s) |

TABLE 1-continued

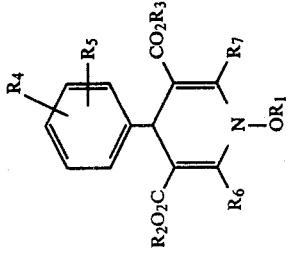

| Compound No. | $R_1$ | $R_2$ | $R_3$ | $R_4$ | $R_5$ | $R_6$ | $R_7$ | m.p. °C. | NMR · δ |
|---|---|---|---|---|---|---|---|---|---|
| 16 | H | $CH_3$ | $CH(CH_3)_2$ | 2-Cl | 3-Cl | $CH_3$ | $CH_3$ | (amorphous) | $CCl_4$:1.13(6H,d,d), 2.34(6H,s), 3.57(3H,s), 4.6-5.1(1H,m), 5.32(1H,s), 6.6-7.3(3H,m), 8.57(1H,s) |
| 17 | H | $CH_3$ | ![NH-piperidine] | H | 3-$NO_2$ | $CH_3$ | $CH_3$ | (amorphous) | DMSO—$d_6$:1.0-2.2(4H,broad), 2.48(6H,s), 2.7-3.3(4H,broad), 3.64(3H,s), 4.7-5.2(1H,broad), 5.13(1H,s), 7.0-8.5(5H,m) |
| 18 | H | $CH_3$ | ![N-H piperidine] | H | 3-$NO_2$ | $CH_3$ | $CH_3$ | (amorphous) | DMSO—$d_6$:1.1-2.0(4H,broad), 2.47(6H,s), 2.7-3.4(4H,broad), 3.60(3H,s), 4.7-5.2(1H,broad), 5.12(1H,d), 7.0-8.4(5H,m) |
| 19 | H | $CH_3$ | ![N-CH2-phenyl piperidine .HCl] | H | 3-$NO_2$ | $CH_3$ | $CH_3$ | 227-229 | $CDCl_3$(HCl free):1.4-2.0 (4H,broad), 2.1-2.9(10H, broad),3.43(2H,s), 3.69 (3H,s), 4.5-5.0(1H,broad), 5.20(1H,s), 7.23(5H,s), 7.3-8.2(5H,m) |
| 20 | H | $CH_3$ | ![N-CH2-phenyl piperidine .HCl] | H | 3-$NO_2$ | $CH_3$ | $CH_3$ | (amorphous) | DMSO—$d_6$(HCl free):1.0-2.0 (4H,broad), 2.0-2.9(4H, broad), 2.49(6H,s), 3.2-3.8 (5H,m), 4.5-5.0(1H,broad), 5.13(1H,s), 7.60(5H,d), 7.4-8.3(4H,m) |

TABLE 1-continued

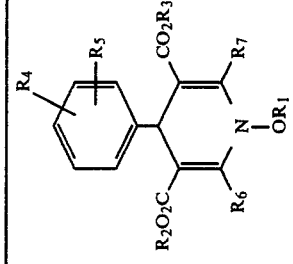

| Compound No. | $R_1$ | $R_2$ | $R_3$ | $R_4$ | $R_5$ | $R_6$ | $R_7$ | m.p. °C. | NMR · δ |
|---|---|---|---|---|---|---|---|---|---|
| 21 | H | $CH_3$ | $CH_2CH_2N(CH_3)CH_2$-C$_6$H$_5$·HCl | H | 3-$NO_2$ | $CH_3$ | $CH_3$ | (amorphous) | $CCl_4$(HCl free): 2.08(3H,s), 2.41(6H,s), 2.55(2H,broad), 3.38(2H,s), 3.54(3H,s), 4.08(2H,broad), 5.07(1H,s), 7.00(5H,s), 7.2–8.0(5H,m) |
| 22 | $CH_3$ | $CH_3$ | $CH_3$ | H | 3-$NO_2$ | $CH_3$ | $CH_3$ | 100–101 | DMSO—$d_6$:2.50(6H,s), 3.68(6H,s), 3.77(3H,s), 5.19(1H,s), 7.5–8.2(4H,m) |
| 23 | $CH_2$-C$_6$H$_5$ | $CH_3$ | $CH_3$ | H | 3-$NO_2$ | $CH_3$ | $CH_3$ | 128–130 | DMSO—$d_6$:2.51(6H,s), 3.69(6H,s), 4.90(2H,s), 5.22(1H,s), 7.39(5H,s), 7.5–8.3(4H,m) |
| 24 | $CH_2CH=CH_2$ | $CH_3$ | $CH_3$ | H | 3-$NO_2$ | $CH_3$ | $CH_3$ | 123–124.5 | $CDCl_3$:2.56(6H,s), 3.76(6H,s), 4.33(2H,d), 5.1–6.2(4H,m), 7.4–8.2(4H,m) |
| 25 | C—$CH_3$ ‖ O | $CH_3$ | $CH_3$ | H | 3-$NO_2$ | $CH_3$ | $CH_3$ | 105.5–106.5 | $CDCl_3$:2.33(3H,s), 2.38(6H,s), 3.70(6H,s), 5.20(1H,s), 7.4–8.4(4H,m) |

In the description hereinbelow, the compounds of Compound No. 1, 2, 3, ... and 25 are referred to as Compounds 1, 2, 3, ... and 25, respectively.

Results of the hypotensive effect test and vasodilating effect test of the representative examples of the present compounds are shown below.

(1) Hypotensive Effect

Groups, each of which was consisting of 4 mongrel adult dogs (both male and female, weighing 15–20 kg), were anesthetized by intravenously administrating 30 mg/kg of sodium pentobarbital. Each anesthetized dog was fixed in the supine position, and subsequently a cannula was inserted into the femoral artery. The blood pressure was measured with a blood pressure transducer (Nippon Kōden, MPU-0.5) and recorded on a polygraph. Thereafter, a suspension of the test compound in a 0.3% CMC solution was administered via the cannula planted in the duodenum of the anesthetized dog, and the change in blood pressure was observed. The results are given in Table 2.

TABLE 2

| Test Compound | Dose (mg/Kg) | 10 min. | 30 min. | 1 hr. | 2 hrs. | 3 hrs. | 4 hrs. | 5 hrs. |
|---|---|---|---|---|---|---|---|---|
| Compound 1 | 0.3 | −3.7 ±1.5 | −12.8 ±1.9 | −16.4 ±2.6 | −13.3 ±3.4 | −12.8 ±1.9 | −10.6 ±2.3 | −8.9 ±4.0 |
|  | 1.0 | −2.6 ±0.8 | −11.7 ±1.7 | −18.2 ±2.1 | −18.2 ±2.6 | −19.4 ±2.8 | −18.7 ±4.4 | −13.5 ±5.4 |
| Compound 2 | 0.3 | −2.4 ±1.3 | −2.5 ±2.1 | −16.1 ±2.3 | −15.5 ±3.0 | −13.4 ±1.0 | −12.1 ±1.3 | −10.9 ±3.7 |
|  | 1.0 | −3.9 ±0.9 | −11.4 ±3.5 | −18.1 ±2.5 | −23.2 ±3.8 | −22.6 ±4.1 | −20.7 ±4.0 | −18.3 ±5.2 |
| Compound 4 | 0.1 | +0.7 ±1.6 | −10.7 ±3.2 | −22.7 ±4.5 | −23.5 ±6.2 | −21.0 ±7.0 | −21.0 ±7.3 | −19.6 ±8.6 |
|  | 0.3 | −2.5 ±1.0 | −10.3 ±4.4 | −20.8 ±4.8 | −36.9 ±7.3 | −32.4 ±11.1 | −31.3 ±13.2 | −29.5 ±12.4 |
| Compound 8 | 0.3 | −1.7 ±1.6 | −10.8 ±1.4 | −18.0 ±4.2 | −17.4 ±3.6 | −17.3 ±4.3 | −15.2 ±3.8 | −13.3 ±5.6 |
|  | 1.0 | −2.1 ±2.8 | −10.2 ±3.4 | −19.6 ±6.1 | −25.4 ±6.3 | −25.7 ±7.9 | −21.9 ±7.6 | −19.8 ±8.2 |
| Compound 19 | 0.3 | −1.8 ±1.1 | −8.6 ±0.9 | −15.3 ±1.4 | −17.1 ±2.0 | −16.6 ±3.3 | −16.3 ±3.1 | −14.8 ±4.7 |
|  | 1.0 | −0.8 ±1.7 | −9.0 ±2.0 | −17.7 ±4.0 | −20.3 ±3.3 | −19.7 ±4.6 | −18.3 ±5.3 | −17.1 ±4.8 |
| Nifedipine (Comparative Drug) | 0.3 | −7.8 ±4.6 | −12.4 ±4.5 | −18.4 ±6.5 | −15.7 ±9.6 | — | — | — |
|  | 1.0 | −19.0 ±3.4 | −31.3 ±2.5 | −25.0 ±6.7 | −24.3 ±2.0 | −18.5 ±2.4 | −10.6 ±4.2 | −7.3 ±4.2 |

As evident from Table 2, the present compounds have a superior and long-lasting hypotensive effect and thus are compounds useful as hypotensives.

(2) Vasodilating Effect

Groups, each of which was consisting of 3 mongrel adult dogs (both male and female, weighing 15–20 kg), were anesthetized by intravenously administrating 30 mg/kg of sodium pentobarbital. Thereafter, the chest of each anesthetized dog was incised, then probes for measuring the blood flow were fitted to the circumflex branch of left coronary artery, the vertebral artery and the femoral artery, and the blood flow of each artery was measured with a square wave electromagnetic flowmeter (Nippon Kōden).

A suspension of the test compound in a 0.3% CMC solution was administered via a cannula planted in the duodenum of the anesthetized dog. The results are given in Table 3.

TABLE 3

| Test Compound | Dose (mg/kg) | Percent Increase in Blood Flow | | |
|---|---|---|---|---|
| | | Coronary Artery | Vertebral Artery | Femoral Artery |
| Compound 1 | 0.3 | 51 | 42 | 21 |
|  | 1.0 | 59 | 55 | 40 |
| Compound 2 | 0.3 | 25 | 21 | 18 |
|  | 1.0 | 46 | 35 | 30 |
| Compound 4 | 0.1 | 50 | 59 | 23 |
|  | 0.3 | 120 | 85 | 55 |
| Compound 8 | 0.3 | 28 | 18 | 9 |
|  | 1.0 | 45 | 40 | 21 |
| Compound 19 | 0.3 | 30 | 23 | 22 |
|  | 1.0 | 50 | 49 | 38 |

From Table 3, it is obvious that the compounds of the present invention have an excellent effect to increase the blood flow and thus are compounds useful as vasodilators.

The compounds of the present invention, in consideration of their pharmaceutical effect, may be employed in various pharmaceutical forms for the intended administration, and in particular, they are preferably employed in oral forms such as tablets, powders etc.

In the case of tablets, the compound of the present invention may be contained in an amount of 5–30% (W/W) per tablet. As other components (carriers), commonly employed excipients, disintegrants, lubricants, binders, coating agents etc. may be employed.

For example, there may be mentioned excipients such as glucose, lactose etc., disintegrators such as starch, calcium carboxymethyl cellulose etc., lubricants such as magnesium stearate, talc etc., binders such as simple syrup, polyvinyl alcohol, gelatin, hydroxypropyl cellulose etc., and coating agents such as dispersants (e.g. methyl cellulose and ethyl cellulose) and plasticisers (e.g. glycerin and polyethylene glycol). Microcrystalline cellulose partakes of the properties of disintegrators and of excipients.

In the case of powders, the compound of the present invention may be contained in an amount of 1–20% (W/W). As the carriers, excipients such as glucose, lactose etc., binders such as hydroxypropyl cellulose etc., and the like may be employed. The dose is preferably in the range of 1–100 mg per day for a human adult (weighing about 60 kg). Certain specific embodiments of the invention are illustrated by the following representative examples.

The physicochemical properties of the compounds obtained in the following Examples 1–25 are given in Table 1.

EXAMPLE 1

To a mixture of 72.1 g of zinc chloride in 200 ml of ethyl acetate was added dropwise a mixture of 40.0 g of m-nitrobenzaldehyde and 61.5 g of methyl acetoacetate at room temperature over 50 minutes. The mixture was stirred at room temperature for further 15 minutes, and further stirred while heating at 60°–65° C. for 6.5 hours. After completion of the reaction, the reaction mixture was concentrated under reduced pressure, then 800 ml of ether and 800 ml of water were added thereto, and the desired product was extracted with ether. The aqueous layer was extracted again with 300 ml of ether, which was combined with the first ether layer. The combined layer was washed with 200 ml of a 5% aqueous sodium bicarbonate solution, and then with 200 ml of saturated saline. This substance was dried over anhydrous magnesium sulfate, and the ether was distilled off to obtain 92.7 g of crude crystals. The crystals were recrystallized from methanol to obtain 47.7 g (yield 49.3%) of 3,5-bis(methoxycarbonyl)-4-(3-nitrophenyl)-2,6-heptanedione.

m.p.: 94°–96° C.

NMR (CDCl$_3$,δ): 2.10, 2.26(6H in total), 3.52, 3.70(6H in total), 3.97–4.57(3H, m), 7.40–8.30(4H, m)

Thereafter, 2.85 g of hydroxylamine hydrochloride and 1.64 g of sodium hydroxide were stirred in 100 ml of methanol, and the formed sodium chloride was removed by filtration. The filtrate was added dropwise to a mixture of 15.0 g of 3,5-bis-(methoxycarbonyl)-4-(3-nitrophenyl)-2,6-heptanedione in 120 ml of methanol at room temperature over 15 minutes. After stirring the mixture at room temperature for 3 hours, the methanol was distilled off under reduced pressure. Upon addition of 180 ml of ether, a small amount of sodium chloride crystallized out. The crystallized sodium chloride was filtered off, and the ether was distilled off to obtain 14.7 g of crude crystals. The crude crystals were recrystallized from ether:n-hexane (3:1 V/V) to obtain 9.4 g (yield 63.2%) of 1-hydroxy-2,6-dimethyl-4-(3-nitrophenyl)-1,4-dihydropyridine-3,5-dicarboxylic acid dimethyl ester (Compound 1).

EXAMPLES 2–3

By procedures similar to those in Example 1, except that the starting materials used in Example 1 were replaced by those set forth in Table 4, there were obtained 1-hydroxy-2,6-dimethyl-4-(3-nitrophenyl)-1,4-dihydropyridine-3,5-dicarboxylic acid diethyl ester (Compound 2) and 4-(4-chloro-3-nitrophenyl)-1-hydroxy-1,4-dihydropyridine-3,5-dicarboxylic acid dimethyl ester (Compound 3).

TABLE 4

| Example | Starting Material | Amount Used (g) | Desired Product | Yield (g) |
|---|---|---|---|---|
| 2 | m-Nitrobenzaldehyde | 7.55 | Compound 2 | 5.79 |
|  | Ethyl acetoacetate | 13.05 |  |  |
|  | Hydroxylamine hydrochloride | 3.62 |  |  |

TABLE 4-continued

| Example | Starting Material | Amount Used (g) | Desired Product | Yield (g) |
|---|---|---|---|---|
| 3 | 4-Chloro-3-nitrobenzaldehyde | 7.00 | Compound 3 | 6.52 |
|  | Methyl acetoacetate | 8.76 |  |  |
|  | Hydroxylamine hydrochloride | 2.59 |  |  |

EXAMPLE 4

In this example, 14.4 g of isopropyl acetoacetate was dissolved in 60 ml of 1,2-dimethoxyethane and 0.2 g of potassium fluoride was added thereto. The mixture was stirred at room temperature for 30 minutes, and 4.98 g of methyl m-nitrobenzylideneacetoacetate was added thereto. The solution was stirred for 4.5 hours. After completion of the reaction, 200 ml of chloroform and 100 ml of water were added to the reaction mixture to carry out extraction. The extracted chloroform layer was dried over anhydrous sodium sulfate, and then the chloroform and the excess isopropyl acetoacetate were distilled off under reduced pressure to obtain 7.9 g as an oily residue.

Thereafter, a solution of hydroxylamine in methanol obtained from 1.38 g of hydroxylamine hydrochloride, 0.79 g of sodium hydroxide and 60 ml of methanol was added to a solution of 7.9 g of the oily residue obtained above in 50 ml of methanol, and stirred at room temperature for 3.5 hours. After completion of the reaction, the reaction mixture was concentrated under reduced pressure. The concentrate was dissolved in 150 ml of chloroform, then washed with 70 ml of water, and dried over anhydrous sodium sulfate. After drying, the chloroform was distilled off under reduced pressure, and then column chromatography on silica gel (eluent; chloroform:ethanol = 20:1 V/V) was conducted to separate the desired product. The fractions containing the desired product were concentrated, and crystallized from ether-n-hexane to obtain 3.77 g (yield 49.2%) of 1-hydroxy-2,6-dimethyl-4-(3-nitrophenyl)-1,4-dihydropyridine-3,5-dicarboxylic acid 3-isopropyl-5-methyl ester (Compound 4).

EXAMPLES 5–16

By procedures similar to those in Example 4, except that the starting materials used in Example 4 were replaced by those set forth in Table 5, there were obtained 1-hydroxy-2,6-dimethyl-4-(3-nitrophenyl)-1,4-dihydropyridine-3,5-dicarboxylic acid 3-ethyl-5-methyl ester (Compound 5), 1-hydroxy-2,6-dimethyl-4-(3-nitrophenyl)-1,4-dihydropyridine-3,5-dicarboxylic acid 3-methyl-5-n-propyl ester (Compound 6), 1-hydroxy-2,6-dimethyl-4-(3-nitrophenyl)-1,4-dihydropyridine-3,5-dicarboxylic acid 3-isobutyl-5-methyl ester (Compound 7), 1-hydroxy-2,6-dimethyl-4-(3-nitrophenyl)-1,4-dihydropyridine-3,5-dicarboxylic acid 3-ethyl-5-isopropyl ester (Compound 8), 1-hydroxy-2,6-dimethyl-4-(3-nitrophenyl)-1,4-dihydropyridine-3,5-dicarboxylic acid 3-allyl-5-methyl ester (Compound 9), 1-hydroxy-2,6-dimethyl-4-(3-nitrophenyl)-1,4-dihydropyridine-3,5-dicarboxylic acid 3-methoxyethyl-5-methyl ester (Compound 10), 1-hydroxy-2,6-dimethyl-4-(3-nitrophenyl)-1,4-dihydropyridine-3,5-dicarboxylic acid-3-methyl-5-(3-tetrahydrofuryl)ester (Compound 11), 1-hydroxy-2,6-dimethyl-4-(3-nitrophenyl)-1,4-dihydropyridine-3,5-dicarboxylic acid 3-methyl-5-[2-(2-thienyl)ethyl]ester (Compound 12), 1-hydroxy-2,6-dimethyl-4-(3-nitrophenyl)-1,4-dihydropyridine-3,5-dicarboxylic acid 3-(2-chloroethyl)-5-methyl ester (Compound 13), 1-hydroxy-2,6-dimethyl-4-(3-nitrophenyl)-1,4-dihydropyridine-3,5-dicarboxylic acid 3-(1-formyl-4-piperidyl)-5-methyl ester (Compound 14), 1-hydroxy-2,6-dimethyl-4-(3-nitrophenyl)-1,4-dihydropyridine-3,5-dicarboxylic acid 3-(1-formyl-3-piperidyl)-5-methyl ester (Compound 15) and 4-(2,3-dichlorophenyl)-1-hydroxy-2,6-dimethyl-1,4-dihydropyridine-3,5-dicarboxylic acid 3-isopropyl-5-methyl ester (Compound 16).

TABLE 5

| Example | Starting Material | Amount Used (g) | Desired Product | Yield (g) |
|---|---|---|---|---|
| 5 | Methyl m-nitrobenzylideneacetoacetate | 6.23 | Compound 5 | 2.93 |
|   | Ethyl acetoacetate | 13.0 | | |
|   | Hydroxylamine hydrochloride | 1.76 | | |
| 6 | n-Propyl m-nitrobenzylideneacetoacetate | 5.30 | Compound 6 | 2.57 |
|   | Methyl acetoacetate | 11.10 | | |
|   | Hydroxylamine hydrochloride | 1.28 | | |
| 7 | Isobutyl m-nitrobenzylideneacetoacetate | 4.80 | Compound 7 | 3.56 |
|   | Methyl acetoacetate | 9.57 | | |
|   | Hydroxylamine hydrochloride | 1.13 | | |
| 8 | Ethyl m-nitrobenzylideneacetoacetate | 6.58 | Compound 8 | 4.83 |
|   | Isopropyl acetoacetate | 14.4 | | |
|   | Hydroxylamine hydrochloride | 1.74 | | |
| 9 | Allyl m-nitrobenzylideneacetoacetate | 7.00 | Compound 9 | 3.06 |
|   | Methyl acetoacetate | 14.77 | | |
|   | Hydroxylamine hydrochloride | 1.84 | | |
| 10 | Methoxyethyl m-nitrobenzylideneacetoacetate | 4.50 | Compound 10 | 3.07 |
|   | Methyl acetoacetate | 8.91 | | |
|   | Hydroxylamine hydrochloride | 1.11 | | |
| 11 | 3-Tetrahydrofuryl m-nitrobenzylideneacetoacetate | 4.00 | Compound 11 | 1.42 |
|   | Methyl acetoacetate | 7.61 | | |
|   | Hydroxylamine hydrochloride | 0.81 | | |
| 12 | 2-(2-Thienyl)ethyl m-nitrobenzylideneacetoacetate | 8.80 | Compound 12 | 3.03 |
|   | Methyl acetoacetate | 14.8 | | |
|   | Hydroxylamine hydrochloride | 1.02 | | |
| 13 | 2-Chloroethyl m-nitrobenzylideneacetoacetate | 6.54 | Compound 13 | 5.00 |
|   | Methyl acetoacetate | 12.72 | | |
|   | Hydroxylamine hydrochloride | 1.53 | | |
| 14 | m-Nitrobenzylideneacetoacetic acid 1-formyl-4-piperidyl ester | 13.4 | Compound 14 | 12.5 |
|   | Methyl acetoacetate | 22.5 | | |
|   | Hydroxylamine hydrochloride | 2.78 | | |
| 15 | m-Nitrobenzylideneacetoacetic acid 1-formyl-3-piperidyl ester | 5.81 | Compound 15 | 5.40 |
|   | Methyl acetoacetate | 9.74 | | |
|   | Hydroxylamine | 1.15 | | |
| 16 | Methyl 2,3-dichlorobenzylideneacetoacetate | 5.0 | Compound 16 | 2.80 |
|   | Isopropyl acetoacetate | 10.2 | | |
|   | Hydroxylamine hydrochloride | 1.35 | | |

EXAMPLE 17

A mixture of 10.4 g of Compound 14 obtained in Example 14, 4.75 g of p-toluenesulfonic acid, 36 ml of methanol and 36 ml of ethanol was stirred under reflux for 7 hours and the reaction mixture was diluted with 120 ml of water, and the dilute solution was neutralized with a 5% aqueous sodium bicarbonate solution, and extracted with 200 ml, 100 ml and 50 ml of chloroform, respectively. The chloroform layers extracted respectively were combined, washed with water, dried over anhydrous sodium sulfate, and then concentrated to dryness under reduced pressure to obtain 9.8 g (yield 100%) of 1-hydroxy-2,6-dimethyl-4-(3-nitrophenyl)-1,4-dihydropyridine-3,5-dicarboxylic acid 3-methyl-5-(4-piperidyl)ester (Compound 17).

EXAMPLE 18

By procedures similar to those in Example 17, except that Compound 14 used in Example 17 was replaced by 8.9 g of Compound 15, there was obtained 8.37 g of 1-hydroxy-2,6-dimethyl-4-(3-nitrophenyl)-1,4-dihydropyridine-3,5-dicarboxylic acid 3-methyl-5-(3-piperidyl)ester (Compound 18).

EXAMPLE 19

A mixture of 9.8 g of Compound 17 obtained in Example 17, 4.3 g of benzyl chloride, 3.4 g of triethylamine and 120 ml of toluene was stirred under reflux for 7 hours. After completion of the reaction, the reaction mixture was dissolved in 500 ml of chloroform, and washed with 250 ml of water. The resulting washed chloroform layer was dried over anhydrous sodium sulfate, and then the solvent was distilled off under reduced pressure to obtain 16.9 g of an oily residue. The residue was subjected to silica gel chromatography (eluent; chloroform:methanol=15.1 V/V) to separate the desired product. The fractions containing the desired product were concentrated, and then the concentrate was dissolved in a mixed solvent of 30 ml of acetone and 10 ml of water. Thereafter, 26 ml of 1N hydrochloric acid was added thereto and the mixture was stirred, whereby yellow crystals were separated out. The crystals were collected by filtration, washed with water and dried to obtain 4.1 g (yield 33.1%) of 1-hydroxy-2,6-dimethyl-4-(3-nitrophenyl)-1,4-dihydropyridine-3,5-dicarboxylic acid 3-(1-benzyl-4-piperidyl)-5-methyl ester hydrochloride (Compound 19).

EXAMPLE 20

By procedures similar to those in Example 19, except that Compound 17 and 4.3 g of the benzyl chloride were replaced by 8.31 g of Compound 18 and 2.66 g of benzyl chloride, there was obtained 3.78 g of 1-hydroxy-2,6-dimethyl-4-(3-nitrophenyl)-1,4-dihydropyridine-3,5-dicarboxylic acid 3-(1-benzyl-4-piperidyl)-5-methyl ester hydrochloride (Compound 20).

EXAMPLE 21

In this example, 3.2 g of Compound 13 obtained in Example 13 was dissolved in 24 ml of acetonitrile, and to the solution was added 2.3 g of sodium iodide. The mixture was stirred under reflux in $N_2$ atmosphere for 7.5 hours. After completion of the reaction, the reaction mixture was cooled, then the crystallized salt was filtered off, and the filtrate was concentrated. The concentrate was dissolved in 30 ml of toluene, and to the solution was added 2.34 g of N-methylbenzylamine. The mixture was stirred at 80°–90° C. under $N_2$ atmosphere for 13 hours. After completion of the reaction, the reacton mixture was diluted with 80 ml of ethyl acetate, then washed with a 10% aqueous citric acid solution and water, and dried over anhydrous sodium sulfate. The solvent was distilled off under reduced pressure, and column chromatography on silica gel (eluent; chloroform:methanol=20:1 V/V) was conducted to separate the desired product. The fractions containing the desired product were concentrated, dissolved in 6 ml of ethyl acetate, and 1 ml of ether saturated with hydrogen chloride was added thereto. The solution was concentrated to dryness to obtain 1.12 g (yield 26.5%) of 1-hydroxy-2,6-dimethyl-4-(3-nitrophenyl)-1,4-dihydropyridine-3,5-dicarboxylic acid 3-[2-(N-benzyl-N-methylamino)ethyl]ester-5-methylester hydrochloride (Compound 21).

EXAMPLE 22

In this example, 4.00 g of Compound 1 obtained in Example 1 was dissolved in 40 ml of methanol, and 2.34 g of soidum methylate (28% methanol solution) was added to the solution. Thereafter, a solution of 1.53 g of dimethyl sulfate in 20 ml of methanol was added thereto dropwise at room temperature over 10 minutes. Stirring was effected at room temperature for further 2 hours, and the reaction mixture was cooled to obtain 2.83 g (yield 68.0%) of 2,6-dimethyl-1-methoxy-4-(3-nitrophenyl)-1,4-dihydropyridine-3,5-dicarboxylic acid dimethyl ester (Compound 22).

EXAMPLE 23

In this example, 2.00 g of Compound 1 obtained in Example 1 was dissolved in 20 ml of tetrahydrofuran, and then to the solution were added 0.46 g of sodium hydroxide and 1.40 g of benzyl chloride. Stirring was effected at room temperature for 7 hours, and the reaction mixture was concentrated under reduced pressure. To the concentrate were added 15 ml of chloroform and 15 ml of water to carry out extraction. The extracted chloroform layer was washed with water, then dried over anhydrous sodium sulfate, and was concentrated under reduced pressure to obtain crude crystals. Then, the crystals were recrystallized from methanol to obtain 1.52 g (yield 60.8%) of 1-benzyloxy-2,6-dimethyl-4-(3-nitrophenyl)-1,4-dihydropyridine-3,5-dicarboxylic acid dimethyl ester (Compound 23).

EXAMPLE 24

By procedures similar to those in Example 23, except that 1.40 g of the benzyl chloride was replaced by 1.33 g of allyl bromide, there was obtained 1.61 g (yield 72.5%) of 1-allyloxy-2,6-dimethyl-4-(3-nitrophenyl)-1,4-dihydropyridine-3,5-dicarboxylic acid dimethyl ester (Compound 24).

EXAMPLE 25

In this example, 1.42 g of pyridine was added to a solution of 5.00 g of Compound 1 obtained in Example 1 in 25 ml of tetrahydrofuran, and the mixture was cooled to $-10°$ C. or below. To the solution was added dropwise a solution of 1.25 g of acetyl chloride in 10 ml of tetrahydrofuran while keeping the temperature not higher than $-10°$ C. Further, stirring was continued at $-10°$ C. or below whereby crystals were deposited. 2.5 Hours later, 40 ml of water was added thereto, and the mixture was stirred with ice cooling for 1.5 hours. Thereafter, the crystals were collected by filtration, washed with water and dried to obtain 4.14 g (yield 74.2%) of 1-acetoxy-2,6-dimethyl-4-(3-nitrophenyl)-1,4-dihydropyridine-3,5-dicarboxylic acid dimethyl ester (Compound 25).

EXAMPLE 26

(Example of Preparation of 10,000 10-mg Tablets)

| | |
|---|---|
| Compound 4 | 100 g |
| Magnesium stearate | 4 g |
| Microcrystalline cellulose | 796 g |

The above components were mixed on a mixer for 5 minutes. The mixed powder was compressed on a tabletting machine (Kikusui Seisakusho, Model HU-37) using round-cornered flat punches of 6.0 mm in a diameter to obtain 10,000 tablets of 6.0 mm in a diameter, 2.5 mm in thickness and 90 mg in weight.

EXAMPLE 27

(Example of Preparation of Powder)

| | |
|---|---|
| Compound 1 | 110 g |
| Lactose | 870 g |
| Hydroxypropyl cellulose | 20 g |

Using an aqueous solution of hydroxypropyl cellulose as a binder, Compound 1 and lactose were granulated on a fluidized bed pelletizer.

What is claimed is:

1. A 1,4-dihydropyridine compound having the general formula:

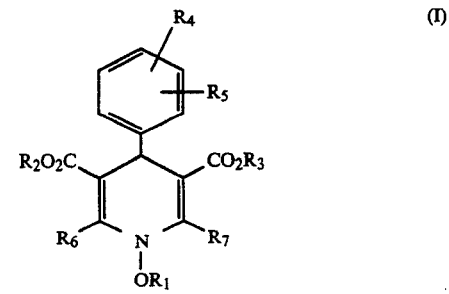

wherein $R_1$ represents a hydrogen atom, an alkyl group having 1-5 carbon atoms, an alkenyl group having 2-5 carbon atoms, a benzyl group, a phenethyl group, a diphenylmethyl group, a formyl group, an acetyl group, a pivaloyl group or a benzoyl group, $R_2$ and $R_3$ are the same or different groups and each represents a substituted or unsubstituted alkyl group having 1-5 carbon atoms wherein the substituents include a halogen atom and an alkoxy group having 1-5 carbon atoms, an alkenyl group having 2-5 carbon atoms, a disubstituted aminoalkyl group having 1-5 carbon atoms wherein substituents are the same or different groups and include alkyl groups having 1-5 carbon atoms, and a benzyl group or a substituted or unsubstituted heterocyclic group wherein the heterocyclic group includes a thienyl group, a furyl group, a piperidyl group, a pyranyl group, and a pyrrolidinyl group; and the substituent includes a hydrogen atom, an alkyl group having 1-5 carbon atoms, a benzyl group, a phenethyl group, a formyl group, an acetyl group and benzoyl group, $R_4$ and $R_5$ are the same or different groups and each represents a hydrogen atom, a halogen atom or a nitro group, and $R_6$ and $R_7$ are the same or different groups and each represents an alkyl group having 1-5 carbon atoms; or a pharmaceutically acceptable acid addition salt thereof.

2. A compound according to claim 1, namely, 1-hydroxy-2,6-dimethyl-4-(3-nitrophenyl)-1,4-dihydropyridine-3,5-dicarboxylic acid dimethyl ester.

3. A compound according to claim 1, namely, 1-hydroxy-2,6-dimethyl-4-(3-nitrophenyl)-1,4-dihydropyridine-3,5-dicarboxylic acid diethyl ester.

4. A compound according to claim 1, namely, 4-(4-chloro-3-nitrophenyl)-1-hydroxy-1,4-dihydropyridine-3,5-dicarboxylic acid dimethyl ester.

5. A compound according to claim 1, namely, 1-hydroxy-2,6-dimethyl-4-(3-nitrophenyl)-1,4-dihydropyridine-3,5-dicarboxylic acid 3-isopropyl-5-methyl ester.

6. A compound according to claim 1, namely, 1-hydroxy-2,6-dimethyl-4-(3-nitrophenyl)-1,4-dihydropyridine-3,5-dicarboxylic acid 3-ethyl-5-methyl ester.

7. A compound according to claim 1, namely, 1-hydroxy-2,6-dimethyl-4-(3-nitrophenyl)-1,4-dihydropyridine-3,5-dicarboxylic acid 3-methyl-5-n-propyl ester.

8. A compound according to claim 1, namely, 1-hydroxy-2,6-dimethyl-4-(3-nitrophenyl)-1,4-dihydropyridine-3,5-dicarboxylic acid 3-isobutyl-5-methyl ester.

9. A compound according to claim 1, namely, 1-hydroxy-2,6-dimethyl-4-(3-nitrophenyl)-1,4-dihydropyridine-3,5-dicarboxylic acid 3-ethyl-5-isopropyl ester.

10. A compound according to claim 1, namely, 1-hydroxy-2,6-dimethyl-4-(3-nitrophenyl)-1,4-dihydropyridine-3,5-dicarboxylic acid 3-allyl-5-methyl ester.

11. A compound according to claim 1, namely, 1-hydroxy-2,6-dimethyl-4-(3-nitrophenyl)-1,4-dihydropyridine-3,5-dicarboxylic acid 3-methoxy-ethyl-5-methyl ester.

12. A compound according to claim 1, namely, 1-hydroxy-2,6-dimethyl-4-(3-nitrophenyl)-1,4-dihydropyridine-3,5-dicarboxylic acid 3-methyl-5-(3-tetrahydrofuryl)ester.

13. A compound according to claim 1, namely, 1-hydroxy-2,6-dimethyl-4-(3-nitrophenyl)-1,4-dihydropyridine-3,5-dicarboxylic acid 3-methyl-5-[2-(2-thienyl)ethyl]ester.

14. A compound according to claim 1, namely, 1-hydroxy-2,6-dimethyl-4-(3-nitrophenyl)-1,4-dihydropyridine-3,5-dicarboxylic acid 3-(2-chloroethyl)-5-methyl ester.

15. A compound according to claim 1, namely, 1-hydroxy-2,6-dimethyl-4-(3-nitrophenyl)-1,4-dihydropyridine-3,5-dicarboxylic acid 3-(1-formyl-4-piperidyl)-5-methyl ester.

16. A compound according to claim 1, namely, 1-hydroxy-2,6-dimethyl-4-(3-nitrophenyl)-1,4-dihydropyridine-3,5-dicarboxylic acid 3-(1-formyl-3-piperidyl)-5-methyl ester.

17. A compund according to claim 1, namely, 4-(2,3-dichlorophenyl)-1-hydroxy-2,6-dimethyl-1,4-dihydropyridine-3,5-dicarboxylic acid 3-isopropyl-5-methyl ester.

18. A compound according to claim 1, namely, 1-hydroxy-2,6-dimethyl-4-(3-nitrophenyl)-1,4-dihydropyridine-3,5-dicarboxylic acid-3-methyl-5-(4-piperidyl)ester.

19. A compound according to claim 1, namely, 1-hydroxy-2,6-dimethyl-4-(3-nitrophenyl)-1,4-dihydropyridine-3,5-dicarboxylic acid-3-methyl-5-(3-piperidyl)ester.

20. A compound according to claim 1, namely, 1-hydroxy-2,6-dimethyl-4-(3-nitrophenyl)-1,4-dihydropyridine-3,5-dicarboxylic acid-3-(1-benzyl-4-piperidyl)-5-methyl ester hydrochloride.

21. A compound according to claim 1, namely, 1-hydroxy-2,6-dimethyl-4-(3-nitrophenyl)-1,4-dihydropyridine-3,5-dicarboxylic acid-3-(1-benzyl-4-piperidyl)-5-methyl ester hydrochloride.

22. A compound according to claim 1, namely, 1-hydroxy-2,6-dimethyl-4-(3-nitrophenyl)-1,4-dihydropyridine-3,5-dicarboxylic acid-3-[2-(N-benzyl-N-methylamino)ethyl]ester-5-methyl ester hydrochloride.

23. A compound according to claim 1, namely, 2,6-dimethyl-1-methoxy-4-(3-nitrophenyl)-1,4-dihydropyridine-3,5-dicarboxylic acid dimethyl ester.

24. A compound according to claim 1, namely, 1-benzyloxy-2,6-dimethyl-4-(3-nitrophenyl)-1,4-dihydropyridine-3,5-dicarboxylic acid dimethyl ester.

25. A compound according to claim 1, namely, 1-allyloxy-2,6-dimethyl-4-(3-nitrophenyl)-1,4-dihydropyridine-3,5-dicarboxylic acid dimethyl ester.

26. A compound according to claim 1, namely, 1-acetoxy-2,6-dimethyl-4-(3-nitrophenyl)-1,4-dihydropyridine-3,5-dicarboxylic acid dimethyl ester.

27. An anti-hypertensive or vasodilating composition comprising a pharmaceutical carrier and as active ingredient, an effective amount of a 1,4-dihydropyridine compound of the general formula:

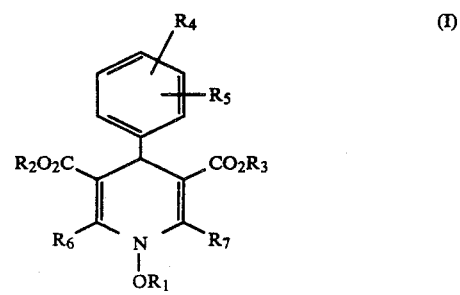

wherein $R_1$ represents a hydrogen atom, an alkyl group having 1–5 carbon atoms, an alkenyl group having 2–5 carbon atoms, a benzyl group, a phenethyl group, a diphenylmethyl group, a formyl group, an acetyl group, a pivaloyl group or a benzoyl group, $R_2$ and $R_3$ are the same or different groups and each represents a substituted or unsubstituted alkyl group having 1–5 carbon atoms wherein the substituents include a halogen atom and an alkoxy group having 1–5 carbon atoms, an alkenyl group having 2–5 carbon atoms, a disubstituted aminoalkyl group having 1–5 carbon atoms wherein substituents are the same or different groups and include alkyl groups having 1–5 carbon atoms, and a benzyl group or a substituted or unsubstituted heterocyclic group wherein the heterocyclic group includes a thienyl group, a furyl group, a piperidyl group, a pyranyl group, and a pyrrolidinyl group; and the substituent includes a hydrogen atom, an alkyl group having 1–5 carbon atoms, a benzyl group, a phenethyl group, a formyl group, an acetyl group and benzoyl group, $R_4$ and $R_5$ are the same or different groups and each represents a hydrogen atom, a halogen atom or a nitro group, and $R_6$ and $R_7$ are the same or different groups and each represents an alkyl group having 1–5 carbon atoms; or a pharmaceutically acceptable acid addition salt thereof.

* * * * *